(12) United States Patent
Harrison et al.

(10) Patent No.: US 7,086,403 B2
(45) Date of Patent: Aug. 8, 2006

(54) CONDOM WITH MALE GENITAL DESENSITIZER LUBRICANT

(75) Inventors: Michael J. Harrison, Princeton, NJ (US); Dennis Blum, Carteret, NJ (US); Gisela McBride, Bordentown, NJ (US); Stephen L. Coulter, Yardley, PA (US); Peter A. Burke, Skillman, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 328 days.

(21) Appl. No.: 10/002,442

(22) Filed: Nov. 15, 2001

(65) Prior Publication Data

US 2002/0103414 A1 Aug. 1, 2002

Related U.S. Application Data

(60) Provisional application No. 60/251,486, filed on Dec. 5, 2000.

(51) Int. Cl.
*A61F 6/04* (2006.01)

(52) U.S. Cl. ...................... 128/844; 128/918

(58) Field of Classification Search ............... 128/842, 128/844, 918; 604/347–353
See application file for complete search history.

(56) References Cited

U.S. PATENT DOCUMENTS

| | | | |
|---|---|---|---|
| 3,363,624 A | 1/1968 | Fishman | 128/132 |
| 4,626,286 A * | 12/1986 | Lubbs | 106/157 |
| 4,829,991 A | 5/1989 | Boeck | 128/79 |
| 4,840,188 A | 6/1989 | Heidenfleder | 128/844 |
| 4,869,270 A | 9/1989 | Ueno | 128/844 |
| 4,869,723 A * | 9/1989 | Harmon | 128/844 |
| 4,956,184 A * | 9/1990 | Kross | 424/661 |
| 5,024,852 A | 6/1991 | Busnel | 427/2 |
| 5,163,448 A | 11/1992 | Foldesy | 158/844 |
| 5,208,031 A | 5/1993 | Kelly | 424/412 |
| 5,314,917 A | 5/1994 | Michaels et al. | 514/556 |
| 5,333,621 A | 8/1994 | Denzer | 128/844 |
| 5,407,919 A | 4/1995 | Brode et al. | 514/57 |
| 5,482,053 A * | 1/1996 | Kelly | 128/918 |
| 5,512,289 A * | 4/1996 | Tseng | 424/426 |
| 5,577,514 A | 11/1996 | Zimmerman | 128/844 |
| 5,624,675 A | 4/1997 | Kelly | 424/405 |
| 5,626,149 A | 5/1997 | Schwartz | 128/842 |
| 5,741,511 A | 4/1998 | Lee | 424/449 |
| 5,785,054 A | 7/1998 | Kelly | 128/842 |
| 5,878,747 A | 3/1999 | Enomoto | 128/844 |
| 5,939,485 A | 8/1999 | Bromberg et al. | 524/556 |

(Continued)

OTHER PUBLICATIONS

Facsimile letter from Peter Schechter of Darby & Darby, to Michael J. Harrison, PH.D., dated Oct. 20, 2004.

(Continued)

*Primary Examiner*—Michael A. Brown
(74) *Attorney, Agent, or Firm*—Kenneth Watov; Kenneth L. Cage; Stephen B. Shear

(57) ABSTRACT

A condom having a first lubricating composition containing a male genitalia desensitizing agent on the inside surface thereof and a second lubricating composition on the outside surface thereof. The first lubricating composition has a higher viscosity than the second lubricating composition so that the first lubricating composition remains on the inside surface of the condom during packaging, shipping, storage, and use.

17 Claims, 3 Drawing Sheets

U.S. PATENT DOCUMENTS

| | | | |
|---|---|---|---|
| 5,979,447 A | 11/1999 | Al-Falahe | 128/842 |
| 6,007,836 A | 12/1999 | Denzer | 424/449 |
| 6,080,100 A | 6/2000 | Bendis | 600/38 |
| 6,095,145 A | 8/2000 | Sadlo | 128/844 |
| 6,297,278 B1 | 10/2001 | Michaels et al. | 514/556 |
| 6,596,401 B1 * | 7/2003 | Terry | 428/447 |

OTHER PUBLICATIONS

International Search Report, dated Jun. 13, 2002—WO 02/045573 A3.

Combined Search and Examination Report, dated Jul. 4, 2005.

Facsimile letter to Stephen Shear from Darby & Darby, dated Jun. 29, 2005.

Facsimile letter to Stephen Shear from Darby & Darby, dated Jun. 30, 2005.

Facsimile letter to Stephen Shear from Darby & Darby, dated Oct. 20, 2004.

Facsimile letter to Stephen Shear from Darby & Darby, dated Jun. 29, 2005.

Facsimile letter to Stephen Shear from Darby & Darby, dated Sep. 23, 2005.

Facsimile letter to Stephen Shear from Darby & Darby, dated Sep. 27, 2005.

Letter to Peter Schechter from Church & Dwight, dated Sep. 27, 2005.

Facsimile letter to Stephen Shear from Darby & Darby, dated Sep. 30, 2005.

* cited by examiner

CONDOM WITH MALE GENITAL DESENSITIZER LUBRICANT

RELATED APPLICATION

This Application is related to co-pending Provisional Application Ser. No. 60/251,486 filed Dec. 5, 2000, for "Condom With Male Genital Desensitizer Lubricant", and takes priority therefrom. The related Application is owned by the same Assignee herewith.

FIELD OF THE INVENTION

The field of the present invention relates generally to condoms, and more specifically to condoms having a lubricant system which includes a genital desensitizing agent and controls the application thereof to male genitalia.

BACKGROUND OF THE INVENTION

Much effort has been made to provide a composition containing a male desensitization agent suitable for preventing premature ejaculation. Many of these compositions provide a water-based lubricant with benzocaine as the active component at a concentration of from about 3% to 7.5%. Such compositions are inconvenient to use, in that they require direct application to the male genitalia prior to intercourse. In addition, these compositions typically expose the female partner to the composition and its desensitizing effects with such exposure being highly undesirable.

Heidenfelder, (U.S. Pat. No. 4,840,188) discloses the coating of the interior surface of a condom with a local anesthetic such as benzocaine to provide desensitization. The location of the desensitizing agent on the interior surface of the condom provides advantages over direct application products.

Despite these efforts, there is still a need to provide a condom with desensitizing capability that can be readily employed without risk of exposure to the female partner and still provide the benefits of a lubricating composition.

SUMMARY OF THE INVENTION

The present invention generally provides a condom that incorporates two distinct lubricating compositions. One such composition is a relatively high viscosity lubricant composition containing at least one desensitizing agent that is bottom shot into the interior of a nipple up condom to coat the interior surfaces thereof. A second, lower viscosity lubricant composition containing no desensitizing agent is top shot on the outside of the condom prior to, or at the same time as following the application of the bottom shot lubricant composition. The high viscosity lubricant composition with a desensitizing agent remains substantially in place during packing, shipping, storage, and use so that the full benefits of continuous contact with the desensitizing agent can be realized. In this manner, separation of the first lubricant composition containing the desensitizing agent from the exterior surfaces of the condom is maximized in order to minimize contact with the female partner and thereby avoid desensitization of the female genitalia.

In one aspect of the present invention there is provided a condom comprising:

a male genital engaging tubular sheath having an inner surface and an outer surface;

a first lubricant composition comprising an effective amount of a male genital desensitizing agent located on at least a portion of the interior surface of the tubular sheath, said first lubricant composition having a relatively high viscosity sufficient to maintain the first lubricant composition on the inner surface of the condom during packaging, shipping, storage, and use; and a second lubricant composition containing no desensitizing agent and having a lower viscosity than the first lubricant composition, the second lubricant composition being located on the outside surface of the tubular sheath.

In a preferred form of the invention, the first lubricant composition has a viscosity of from about 10,000 to 75,000 cps, while the second lubricant composition has a viscosity of from about 500 to 20,000 cps.

BRIEF DESCRIPTION OF THE DRAWING

Various embodiments of the present invention are described below with reference to the drawings, in which like items are identified by the same reference designation, wherein.

DETAILED DESCRIPTION OF THE INVENTION

Figure 1:
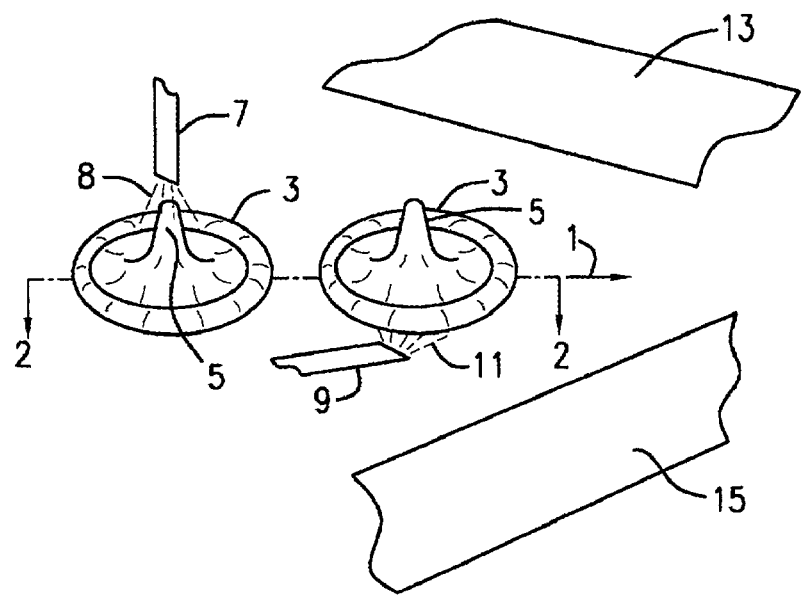
FIG. 1 is a schematic diagram showing a method of applying the first lubricant composition to the interior portion of a condom and the second lubricant composition to the exterior portion of the condom for one embodiment of the invention.

In one embodiment of the present invention, the interior surface of a condom is lubricated with a first lubricant composition containing a relatively high viscosity lubricant composition along with at least one male genital desensitizing agent.

As used herein the term "desensitizing agent" means any material including topical anesthetics that reduce the sensitivity of male genitalia in a manner which may prevent premature ejaculation. Examples of suitable desensitizing agents include benzocaine, butambin picrate, dibucaine, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor camphorated metacresol, juniper tar, menthol, phenol, phenolate sodium, resorcinol, diphenhydramine hydrochloride, tripelennamine hydrochloride, and combinations thereof. The preferred desensitizing agent is benzocaine.

The desensitizing agent may be present in the first lubricating composition in a desensitizing effective amount which may be typically from about 0.5 to 25% by weight based on the total weight of the of the composition, preferably from about 3 to 7.5% by weight. In a preferred composition the desensitizing agent is benzocaine in an amount of about 6.0% by weight. It will be understood that the selection of an effective amount of the desensitizing agent is within the skill of the art and will depend in part on the particular desensitizing agent chosen and the type of other components of the first lubricating composition.

The type of lubricants which may be used in the first lubricant composition are selected to provide a relatively high viscosity to the composition. The viscosity should be sufficient to enable the first lubricant composition to be applied to the inner surface of the condom and retained thereon during packaging, shipping, storage, and use without splashing and/or splattering.

The first lubricant composition will typically have a viscosity of from about 10,000 to 75,000 cps at ambient temperatures, preferably from about 10,000 to 25,000 cps. In addition, it is desirable that the lubricant be able to solubilize the desensitizing agent to provide uniform distribution of the same over the inner surface of the condom. Typically, lubricants which may be effectively employed in the first lubricating composition could include but are not limited to glycols (e.g. polyethylene glycols, propylene glycol), water-based gels (e.g. glyceryl polymethacrylate, carboxymethyl cellulose), silicone-based oil and gels, mineral oils, and so forth.

The second lubricating composition which is applied only to the exterior surface of the condom, does not contain a desensitizing agent. The viscosity of the second lubricating composition is lower than the first lubricating composition and allows the lubricant to be easily spread around the rolled condom to lubricate the outer surface thereof.

The viscosity of the second lubricant is typically in the range of from about 500 to 20,000 cps. The selection of a suitable lubricant will depend on the type of condom material.

Typical lubricants used for the second lubricating composition include, but are not limited to, the same lubricants used for the first lubricating composition but with a lower viscosity.

The first and second lubricating compositions may be employed on condoms having a variety of shapes and/or compositions. Typical condom forming materials include natural rubber latex, synthetic elastomers such as polyurethane and the like., and natural skin, such as a lamb secum. Various shapes of condoms employed in the present invention are exemplified by reference to FIGS. 3–10 as hereinafter described.

Figure 2:
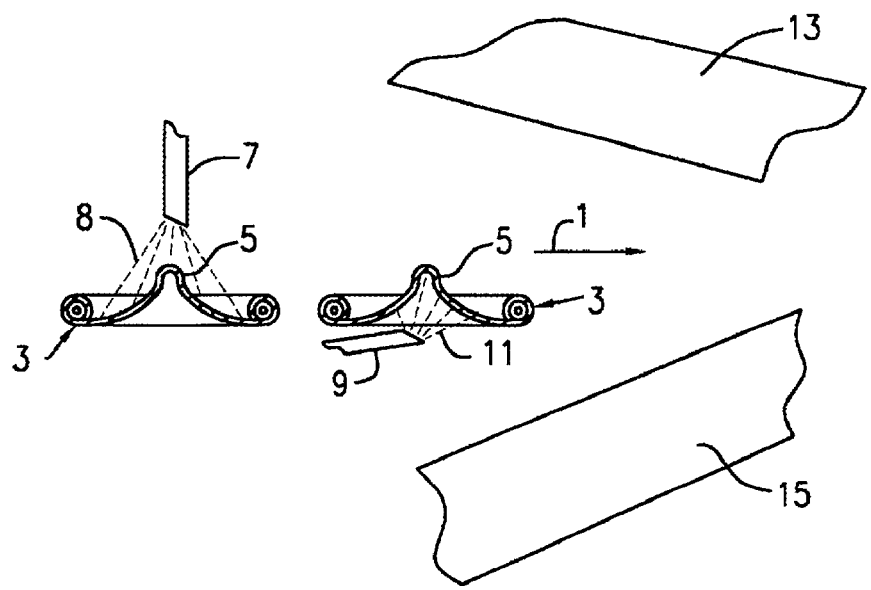
FIG. 2 is a view similar to FIG. 1, the difference being that the condoms are shown in cross section taken along line 2—2 of FIG. 1.

A method of applying the first and second lubricant compositions to a condom will now be described with reference to FIGS. 1 and 2. In one embodiment of the invention, a commercial packaging machine provides an indexed motion in the direction of the arrow 1, for moving rolled condoms 3 in the direction shown. However, in a preferred second embodiment, the motion is not indexed, but rather is timed through the use of rotating cams to activate pumps (not shown) at appropriate times for ejecting associated lubricants from nozzles 7 and 9, for example. This timing embodiment provides for continuous movement of the condoms 3, whereas indexing employs non-continuous movement. The rolled condom 3 with its nipple 5 up first passes beneath a vertical nozzle 7 for applying a relatively low viscosity second lubricating composition 8 on the exterior surfaces of the condom onto and proximate the nipple 5. The condom 3 moves to a position over another nozzle 9 used to apply a first lubricating composition 11 containing a male genital desensitizing agent to the interior or inside surfaces of the condom 3 typically proximate the closed end thereof. The condom 3 which has been provided with the second lubricant composition on the exterior surface of the condom is moved over the lower nozzle 9. After the nozzle 9 is used to apply the first lubricating composition 11 containing a desensitizing agent to the interior surface of the nipple and adjacent areas, the completely lubricated condom 3 then is encapsulated between the two foil layers 13 and 15, and sealed to form a packaged product as is customary in the art of preparing and packaging condoms. Note that in the example of the lubricant application method of FIGS. 1 and 2 the nozzles 7 and 9 are not in the same vertical plane, but are staggered, whereby the lubricants 8 and 11, respectively, are applied at different times. In another embodiment, the nozzles 7 and 9 can be located in the same vertical plane (not shown), whereby lubricants 8 and 11, respectively, would be simultaneously applied.

As previously described, the condoms 3 of the present invention can have any desired shape. Representative examples of various shapes and sizes of suitable condoms 3 are shown in FIGS. 3 through 10. The length of the condoms 3 typically can range from about 160 mm to 220 mm. The nominal length of the condom is typically about 180 mm, with the condom also having a lay-flat width of about 52 mm.

Figure 3:
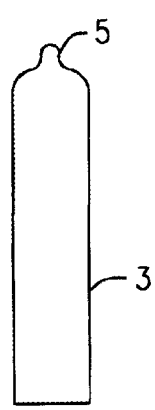
FIGS. 3 through 10 are respective side views of various examples of condoms that can be prepared in accordance with the present invention.
Figure 4:
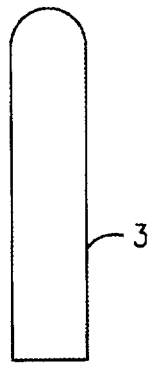
Figure 5:
Figure 6:
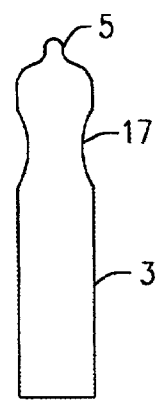
Figure 7:
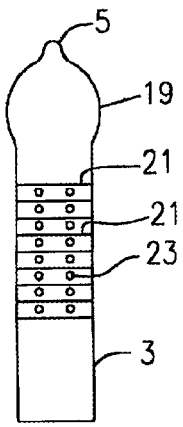
Figure 8:
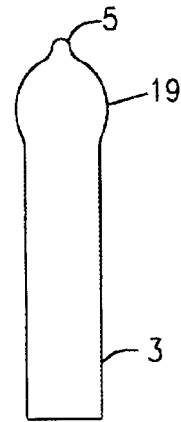
Figure 9:
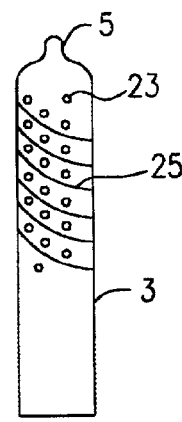
Figure 10:
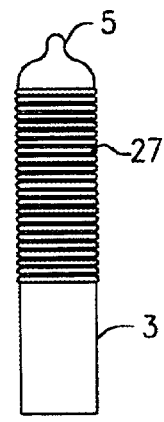

As shown specifically in FIG. 3 the condoms 3 may have parallel walls with a nipple at the closed end, or as shown in FIG. 4 parallel walls without a nipple. The nipple 5 may or may not be included at the closed end. In FIG. 5, the condom 3 has a shape approximating that of a baseball bat. In FIG. 6, the condom 3 includes a tapered portion 17 in its otherwise parallel sidewalls. In FIGS. 7 and 8 the condoms 3 include bulbous lowermost portions 19, with the condom of FIG. 7 also including circular texturing 21 and raised nib portions 23. The configuration of the condom 3 as shown in FIG. 9 includes texturing in the form of spiral ribs 25, along with raised nibs 23. The configuration of the FIG. 10 includes raised successive circular ribs 27. All of the condoms of FIGS. 3–10 and those not specifically disclosed may be treated with the lubricating/desensitizing system of the present invention.

EXAMPLE 1

Preparation of a First Lubricant Composition

A first lubricant composition in accordance with the present invention having the formula shown in Table 1 was prepared as follows:

TABLE 1

| Ingredient | Percent w/w |
| --- | --- |
| Propylene Glycol | 44.0% w/w. |
| Polyethylene Glycol 400 | 15.0% w/w. |
| Lubrajel ® CG* | 35.0% w/w |
| Benzocaine USP | 6.0% w/w |
|  | 100.0% |

*Lubrajel ® is a registered trademark of Guardian Chemical Corporation, Hauppauge, New York and contains glyceryl polymethacrylate, propylene glycol and water.

Figure 11:
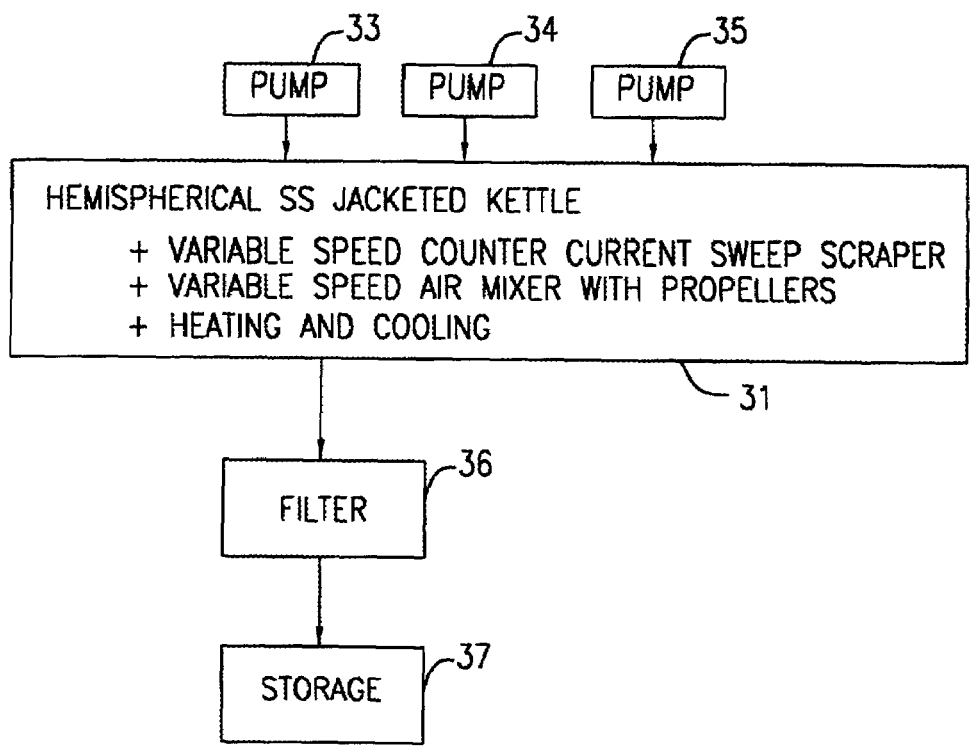
FIG. 11 shows a block diagram of processing equipment for making the first and second lubricant compositions for use in the present invention.

A method for manufacturing the first lubricating composition shown in Table 1 is now be described, with reference to FIG. 11. A hemispherical jacketed kettle 31, is provided with heating and cooling equipment. The kettle is equipped with a variable speed counter current sweep scraper, and a variable speed air mixer with propellers, as known in the art, to provide proper agitation. Three pumps, represented by numerals 33 through 35, are used to charge the kettle 31 with the particular components of the composition shown in Table 1. A Graco FT-14 pump 33 is preferably used to pump the lubricant Lubrajel® CG product into the kettle 31. In certain applications only a single pump 33 may be required due to the very high viscosity of the Lubrajel® CG. Once the first lubricating composition is formed, a 100 mesh SS Triclover type strainer is used to provide a filter 36 for filtering the first lubricating composition prior to placing the same into a storage container 37. Typically, the storage container 37 is provided by a plurality of storage drums constructed of stainless steel, or high density polyethylene, or poly-lined fiber drum.

For the preparation of a batch of about 1,400 kg (kilograms) of the first lubricating composition shown in Table 1, the pumps 33–35 are operated to discharge 616 kg of propylene glycol, 210 kg of polyethylene glycol, and 490 kg of Lubrajel® CG into a 400 gallon capacity kettle 31 from a storage container (not shown), respectively under stirring with a variable speed counter current sweep scraper, and variable speed airmixer with propellers. The contents of the kettle are heated to between 75° C. and 80° C. During heating the air mixer is increased in speed to break up gel bodies and the kettle is charged with 84.0 kg of benzocaine. While maintaining the temperature of the contents of the kettle between 75° C. to 80° C., the mixture is stirred until the gel bodies have dissipated, typically from two to four hours. When the gel bodies have dissipated, the speed of the agitation equipment is decreased, while mixing is continued for a minimum of four hours at a temperature of 75° C. to 80° C.

After mixing as described above, the batch is cooled to between 65° C. and 70° C. When the batch is cooled, it is then discharged from the kettle 31 through the filter 36 into storage drums 37. The viscosity of the thus produced first lubricating composition is in the range of from about 10,000 to 75,000 cps which may be adjusted by altering the amount of the respective starting materials.

EXAMPLE 2

Preparation of Second Lubricating Composition A second lubricating composition containing no desensitizing agent and having the formula shown in Table 2 was prepared in the following manner:

TABLE 2

| Ingredient | Percent w/w |
| --- | --- |
| Proplylene Glycol | 68.20 |
| Polyethylene Glycol 400 | 6.80 |
| Lubrajel ® CG* | 25.00 |
|  | 100.00% |

*Lubrajel ® CG is a registered trademark of Guardian Chemical Corporation and contains glyceryl polymethacrylate, propylene glycol and water.

For the preparation of a batch of about 1,400 kg (kilograms) of the second lubricating composition shown in Table 2, the pumps 33–35 are operated to discharge 954.8 kg of propylene glycol, 95.2 kg of polyethylene glycol, and 350 kg of Lubrajel® CG into a 400 gallon capacity kettle 31 from a storage container (not shown), respectively under stirring with a variable speed counter current sweep scraper, and variable speed airmixer with propellers. The contents of the kettle are heated to between 75° C. and 80° C. During heating the air mixer unit is increased in speed to break up gel bodies. While maintaining the temperature of the contents of the kettle between 75° C. and 80° C., the mixture is stirred until the gel bodies have dissipated, typically from two to four hours. When the gel bodies have dissipated, the speed of the agitation equipment is decreased, while mixing is continued for a minimum of four hours at a temperature of 75° C. to 80° C.

After mixing as described above, the batch is cooled to between 65° C. and 70° C. When the batch is cooled, it is then discharged from the kettle 31 through the filter 36 into storage drums 37. The viscosity of the thus produced first lubricating composition is in the range of from about 500 to 20,000 cps which may be adjusted by altering the amount of the respective ingredients.

Although various embodiments of the invention have been shown and described, they are not intended to limit the invention as encompassed by the claims forming part of the application. Those of skill in the art may recognize certain modifications to these embodiments, which modifications are meant to be covered by the appended claims.

What is claimed is:

1. A condom comprising:
   a male genital engaging tubular sheath having an inner surface and an outer surface;
   a first lubricating composition comprising an effective amount of at least one male genitalia desensitizing agent located on at least a portion of the inner surface of the tubular sheath, said first lubricating composition having a relatively high viscosity sufficient to maintain the first lubricating composition on the inner surface of the condom during packaging and use; and
   a second lubricating composition having a lower viscosity than said first lubricant composition, said second lubricating composition being located on the outside surface of the tubular sheath, wherein the viscosity of said first lubricating composition is from about 10,000 cps to 75,000 cps, and the viscosity of the second lubricating composition is from about 500 cps to 20,000 cps.

2. The condom of claim 1, wherein the viscosity of the first lubricating composition is from about 10,000 cps to 25,000 cps, and the viscosity of the second lubricating composition is from about 2,000 cps to 6,000 cps.

3. The condom of claim 1, wherein the male genitalia desensitizing agent is benzocaine, butambin picrate, dibucaine, dibucaine hydrochloride, dimethisoquin hydrochloride, dyclonine hydrochloride, lidocaine, lidocaine hydrochloride, pramoxine hydrochloride, tetracaine hydrochloride, benzyl alcohol, camphor camphorated metacresol, juniper tar, menthol, phenol, phenolate sodium, resorcinol, diphenhydramine hydrochloride, tripelennamine hydrochloride, and combinations thereof.

4. The condom of claim 1 wherein the male genitalia desensitizing agent is benzocaine.

5. The condom of claim 4, wherein the first lubricating composition comprises about 6% by weight of benzocaine.

6. The condom of claim 5, wherein said first lubricating composition further includes at least one glycol.

7. The condom of claim 1, wherein the first lubricating composition has the following formula:

| | |
| --- | --- |
| Propylene Glycol | 44.0% w/w; |
| Polyethylene Glycol 400 | 15.0% w/w; |
| Mixture of Glyceryl Polymethacrylate, Propylene Glycol and Water | 35.0% w/w; and |
| Benzocaine USP | 6.0% w/w. |

8. The condom of claim 1, wherein said second lubricant composition has the following formula:

| | |
|---|---|
| Propylene Glycol | 68.2% w/w; |
| Polyethylene Glycol 400 | 6.8% w/w; |
| Mixture of Glyceryl Polymethacrylate, Propylene Glycol and Water | 25.0% w/w. |

9. A condom comprising:
 a male genital engaging tubular sheath having an inner surface and an outer surface;
 a first lubricating composition comprising an effective amount of at least one male genitalia desensitizing agent located on at least a portion of the inner surface of the tubular sheath, the viscosity of said first lubricating composition ranging from 10,000 cps to 75,000 cps; and
 a second lubricating composition having a viscosity ranging from 500 cps to 20,000 cps, said second lubricating composition being located on the outside surface of the tubular sheath, and being free of said desensitizing agent.

10. A method for packaging a condom that includes a first lubricating composition containing at least one male genital desensitizing agent on an inside surface thereof, said method comprising:
 rolling a condom having a closed end and respective inside and outside surface to form a circular roll;
 preparing said first lubricating composition having a viscosity of from about 10,000 cps to 75,000 cps;
 placing said first lubricating composition onto the inside surface of the closaed end of said condom to from a lubricated condom;
 preparing a second lubricating composition having no male genitalia desensitizing agent and having a viscosity of from about 500 cps to 20,000 cps;
 placing the second lubricating composition on the outside surface of the condom; and
 packaging said lubricated condom between two foil sheets to form a packaged condom.

11. The method of claim 10, wherein the viscosity of said first lubricating composition is from about 10,000 to 25,000 cps.

12. The method of claim 10, wherein the first lubricating composition contains a desensitiving effective amount of benzocaine as the desensitizing agent.

13. The method of claim 12, wherein the frist lubricating composition comprises about 6% w/w of benzocaine.

14. The method of claim 13, wherein the first lubricating composition further includes at least one glycol.

15. The method of claim 10, wherein the first lubricating composition consists essentially of:

| | |
|---|---|
| Propylene Glycol | 44.0% w/w; |
| Polyethylene Glycol 400 | 15.0% w/w; |
| A Mixture of Glyceryl Polymethacrylate Propylene Glycol and Water | 35.0% w/w; and |
| Benzocaine USP | 6.0% w/w. |

16. The method of claim 10, wherein the second lubricating composition has a viscosity of from about 2,000 cps to 6,000 cps.

17. The method of claim 10, wherein the second lubricanting composition consists essentially of:

| | |
|---|---|
| Propylene Glycol | 68.2% w/w; |
| Polyethylene Glycol 400 | 6.8% w/w; |
| A Mixture of Glyceryl Polymethoacrylate Propylene Glycol and Water | 25.0% w/w. |

* * * * *